United States Patent
Tokunaga et al.

(10) Patent No.: US 9,389,238 B2
(45) Date of Patent: Jul. 12, 2016

(54) AUTOMATIC ANALYZING DEVICE, INFORMATION DISPLAY METHOD THEREOF, AND INFORMATION DISPLAY SYSTEM

(75) Inventors: Tatsuya Tokunaga, Tokyo (JP); Masaki Takano, Tokyo (JP); Toshihide Orihashi, Hitachinaka (JP); Hiroki Mori, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/388,801

(22) PCT Filed: Sep. 16, 2010

(86) PCT No.: PCT/JP2010/066062
§ 371 (c)(1),
(2), (4) Date: Feb. 3, 2012

(87) PCT Pub. No.: WO2011/037069
PCT Pub. Date: Mar. 31, 2011

(65) Prior Publication Data
US 2013/0009988 A1    Jan. 10, 2013

(30) Foreign Application Priority Data
Sep. 28, 2009 (JP) ................ 2009-222625

(51) Int. Cl.
*G06T 11/60* (2006.01)
*G01N 35/00* (2006.01)
(52) U.S. Cl.
CPC .. *G01N 35/00871* (2013.01); *G01N 2035/0091* (2013.01)

(58) Field of Classification Search
CPC ............ G06F 15/00; G09G 5/00; G06T 1/00; G08B 5/00; G01N 35/00; G01N 35/00871; G01N 2035/0091
USPC ......... 345/501, 629, 660, 594, 650, 661, 173, 345/676; 422/63–66; 340/691.6
See application file for complete search history.

(56) References Cited

U.S. PATENT DOCUMENTS

2003/0193525 A1* 10/2003 Nygaard, Jr. .................. 345/810
(Continued)

FOREIGN PATENT DOCUMENTS

| JP | 2007-139792 A | | 6/2007 |
| JP | 2007139792 A | * | 6/2007 |
| JP | 2007232510 A | * | 9/2007 |

(Continued)

*Primary Examiner* — Phi Hoang
*Assistant Examiner* — Michael Le
(74) *Attorney, Agent, or Firm* — Mattingly & Malur, PC

(57) ABSTRACT

An automatic analyzing device has an easy-to-use user interface. In particular, the automatic analyzing device for analyzing samples has a reaction disk to which samples are dispensed conveyed through a conveying path; a control unit that controls movement of the reaction disk; and a display unit that is controlled by the control unit and displays various screens. A sample list including sample IDs and states of analysis of the samples is displayed on a display screen of the display unit so that the sample IDs and the states of analysis can be selected, such that a menu displaying button for displaying processing menus for the sample selected in the sample list is displayed at the sample, and such that options of the menus for the sample are displayed as menu buttons when the menu displaying button is indicated.

14 Claims, 13 Drawing Sheets

(56) References Cited

U.S. PATENT DOCUMENTS

| | | | |
|---|---|---|---|
| 2006/0263905 A1* | 11/2006 | Mishima et al. | 436/520 |
| 2007/0073559 A1* | 3/2007 | Stangel | 705/2 |
| 2007/0078631 A1* | 4/2007 | Ariyoshi et al. | 702/189 |
| 2009/0082984 A1* | 3/2009 | Wakamiya et al. | 702/85 |
| 2009/0148345 A1 | 6/2009 | Hamazumi et al. | |

FOREIGN PATENT DOCUMENTS

| | | | |
|---|---|---|---|
| JP | 2009-036513 A | | 2/2009 |
| JP | 2009-042149 A | | 2/2009 |
| JP | 2009036513 A | * | 2/2009 |
| JP | 2009042149 A | * | 2/2009 |
| JP | 2009-139245 A | | 6/2009 |

* cited by examiner

FIG. 13

| | RACK NO. 1380 | RACK TYPE 1381 | RACK POSITION 1382 | POSITION 1383 | SAMPLE ID 1384 | RACK POSITION STATE 1385 | EXAMINATION ITEM 1386 | RESULT 1387 | PRETREATMENT DISK POSITION 1388 | PRETREATMENT DISK STATE 1389 |
|---|---|---|---|---|---|---|---|---|---|---|
| | G0123 | NORMAL | PRIMARY SAMPLE | 2 | 000100013 | ANALYZING | ALB | 123 | | ANALYZING |
| | | | | | | | CRP | | 25 | COMPLETION OF MEASUREMENT WITH ALARM |
| | | | | | | | AMY | | | |
| | | | | 4 | 000100015 | COMPLETION OF MEASUREMENT WITH ALARM | ALB | 100 | 64 | COMPLETION OF MEASUREMENT |
| | | | | | | | CRP | 90 | | |
| | | | | | | | Na | 852 | 32 | COMPLETION OF MEASUREMENT |
| | | | | | | | Ca | 57 | | |
| | ... | ... | ... | ... | ... | ... | ... | ... | ... | ... |
| | B4567 | EMERGENCY | ACCOMMODATION UNIT | 3 | 000100024 | COMPLETION OF MEASUREMENT | ALB | 98 | 80 | COMPLETION OF MEASUREMENT |
| | | | | | | | AST | 112 | | |
| | | | | | | | GGT | 34 | | |
| | | | | 5 | 000100030 | COMPLETION OF MEASUREMENT | K | 1.6 | NONE | NONE |
| | D8910 | MANUAL RE-EXAMINATION | NONE | 1 | 000100032 | COMPLETION OF MEASUREMENT | GGT | 10.7 | 97 | COMPLETION OF MEASUREMENT |
| | | | | | | | CHOL | 54 | | |

138

AUTOMATIC ANALYZING DEVICE, INFORMATION DISPLAY METHOD THEREOF, AND INFORMATION DISPLAY SYSTEM

TECHNICAL FIELD

The present invention relates to an automatic analyzing device that conducts a qualitative/quantitative analysis for biological samples such as blood and urine, and particularly to a technique for a user interface of an automatic analyzing device having a display screen used for searching and extracting operations necessary in device operations.

BACKGROUND ART

An increasing number of automatic analyzing devices that conduct a qualitative/quantitative analysis for biological samples such as blood and urine have been spread mainly in large-scale hospitals and examination centers due to the promptness and quantitative performance of the analysis. In a conventional automatic analyzing device, the arrangement information, reference numbers, and stock quantity of reagents provided in the device main body are schematically displayed on its display screen. When designating the reagent on the display screen to confirm its states, a confirmation operation for the reagent starts, and the confirmation result is displayed on the display screen. Accordingly, the device becomes more user-friendly for an operator.

For example, Patent Literature 1 discloses a configuration of an automatic analyzing device having a user interface in which there is provided display means that displays the same arrangement states as the actual physical arrangements of sample containers provided on sample trackings or the reagent containers provided on reagent disks, and the display means is controlled to display the type of a designated sample or reagent while discriminating from the others.

Further, among various configurations of automatic analyzing devices, Patent Literature 2 discloses a configuration in which a pretreatment disk is provided and pretreatments such as dilution of samples are performed with the pretreatment disk. However, Patent Literature 2 does not particularly disclose a user interface.

CITATION LIST

Patent Literature

Patent Literature 1: Japanese Patent Application Laid-Open Publication No. 2009-036513
Patent Literature 2: Japanese Patent Application Laid-Open Publication No. 2009-139245

SUMMARY OF INVENTION

Technical Problem

In Patent Literature 1 mentioned above, the display means that displays the same arrangement states as the actual physical arrangements of the sample containers or the reagent containers is provided. When displaying, selected information is displayed using legends and the like so as to be visually discriminated from the others. Further, means that can select each type of legend display is provided and is sensuously or visually displayed on a screen, so that even an inexperienced operator can recognize and perform instinctive operations.

However, in the automatic analyzing device disclosed in Patent Literature 1, displaying a processing menu for a selected sample is not particularly mentioned, and easiness of operations following the selection of a sample while viewing the actual physical arrangements and legends is not particularly considered.

An object of the present invention is to provide an automatic analyzing device having a user-friendly user interface, an information display method thereof, and an information display system.

Solution to Problem

In order to achieve the above-described object, the present invention provides an automatic analyzing device that analyzes samples, the device including: a reaction disk into which samples on sample trackings charged from a charging unit and conveyed through conveying paths are dispensed; a control unit that controls the reaction disk and the like; a display unit that displays the states of the samples processed at the reaction disk; and a storage unit that stores data related to the samples, wherein the control unit controls to display a sample list containing the sample IDs and analysis states of the samples on a display screen of the display unit in a selectable manner, to display a menu display button for displaying a processing menu for the sample selected in the sample list, and to display, if the menu display button is pressed, options of the processing menu for the sample as a menu button.

Further, in order to achieve the above-described object, the present invention provides an automatic analyzing device that analyzes samples, the device including: a reaction disk into which samples on sample trackings charged from a charging unit and conveyed through conveying paths are dispensed; a control unit that controls operations of the reaction disk; a display unit that is controlled by the control unit; and a storage unit that stores data related to the samples, wherein the control unit controls to display on a display screen of the display unit an entire process display area for showing the states of the plural sample trackings in the entire process, and a sample tracking enlarged display area for enlarging the sample tracking selected among the plural sample trackings displayed in the entire process display area, and to display a scroll bar that is arranged near the sample tracking enlarged display area to sequentially display the plural sample trackings.

Further, in order to achieve the above-described object, the present invention provides an automatic analyzing device that analyzes samples, the device including: a pretreatment disk into which samples on sample trackings charged from a charging unit and conveyed through conveying paths are dispensed; a reaction disk into which the samples pretreated at the pretreatment disk are dispensed; a control unit that controls operations of the pretreatment disk and the reaction disk; a display unit that is controlled by the control unit; and a storage unit that stores data related to the samples, wherein the control unit controls to display on a display screen of the display unit an entire process display area for showing the states of the plural sample trackings in the entire process, and a pretreatment disk display area for showing the states of the samples on the pretreatment disk.

Furthermore, in order to achieve the above-described object, the present invention provides an information display system for an automatic analyzing device that analyzes samples, the system including: a storage unit that stores data related to the samples; a display unit that displays information related to an automatic analysis for the samples; and a control unit that controls the storage unit and the display unit, wherein the control unit controls to read the data related to the samples from the storage unit, to display a sample list containing the sample IDs and analysis states of the samples on a display screen of the display unit in a selectable manner, to display a menu display button for displaying a processing menu for the sample selected in the sample list, and to display, if the menu display button is pressed, options of the processing menu for the sample as a menu button.

Likewise, the present invention provides an information display system for an automatic analyzing device that analyzes samples on sample trackings conveyed through conveying paths, the system including: a storage unit that stores data related to the sample trackings; a display unit that displays information related to an automatic analysis for the samples; and a control unit that controls the storage unit and the display unit, wherein the control unit controls: to read the data related to the sample trackings from the storage unit; to display on a display screen of the display unit an entire process display area for showing the states of the plural sample trackings in the entire process, and a sample tracking enlarged display area for enlarging the sample tracking selected among the plural sample trackings displayed in the entire process display area; to display a scroll bar that is arranged near the sample tracking enlarged display area to sequentially display the plural sample trackings; and to read from the storage unit, upon reception of operations of the scroll bar, the data of the sample trackings to be displayed in accordance with the operations of the scroll bar.

Likewise, the present invention provides an information display system for an automatic analyzing device that analyzes samples, the system including: a pretreatment disk into which samples on sample trackings conveyed through conveying paths are dispensed; a storage unit that stores data related to the samples; a display unit that displays information related to an automatic analysis for the samples; and a control unit that controls the pretreatment disk, the storage unit, and the display unit, wherein the control unit controls to display on a display screen of the display unit an entire process display area for showing the states of the plural sample trackings in the entire process, and a pretreatment disk display area for showing the states of the samples on the pretreatment disk.

Advantageous Effects of Invention

According to the present invention, an operator can smoothly and reliably proceed with menu selection for a selected sample in an automatic analyzing device.

BRIEF DESCRIPTION OF DRAWINGS

FIG. 13 is a diagram for showing an example of a data table accumulated in a storage unit of the automatic analyzing device according to the first embodiment.

DESCRIPTION OF EMBODIMENTS

Hereinafter, an embodiment of the present invention will be described using the drawings.

First Embodiment

Figure 1:
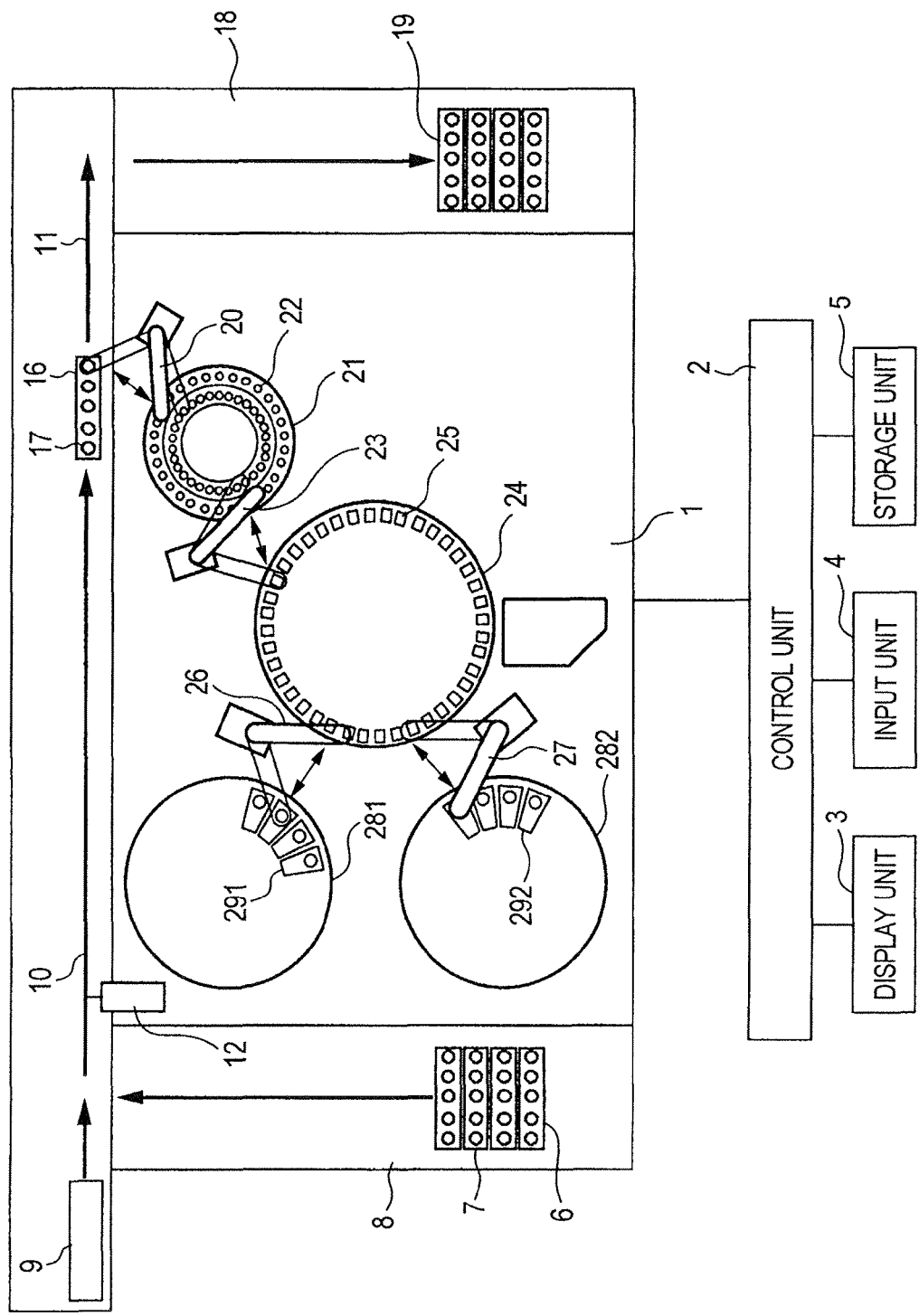
FIG. 1 is a diagram for showing the entire configuration of an automatic analyzing device according to a first embodiment.

FIG. 1 is a diagram for showing the entire configuration of an automatic analyzing device according to a first embodiment. In the drawing, the reference numeral 1 denotes an automatic analyzing device main body whose planar outline configuration is illustrated. The reference numeral 2 denotes a control unit of the device that is a central processing unit (CPU) used for a general personal computer (PC) or the like to control the entire device by executing a program. The reference numeral 3 denotes a display unit such as a flat display represented by a liquid crystal monitor. The reference numeral 4 denotes an input unit such as a mouse and a keyboard, and 5 denotes a storage unit configured using a memory and an external storage device to store programs executed by the control unit 2 and measured data. The control unit 2, the display unit 3, the input unit 4, and the storage unit 5 configure an operation unit of the automatic analyzing device. It should be noted that instead of using the input unit 4, information can be input using the display unit 3 configured as a touch panel or using a graphic user interface (GUI) such as push buttons displayed on a screen of the display unit 3. Thus, these units may be collectively referred to as an input/output unit or a user interface unit.

In the automatic analyzing device main body 1 according to the embodiment, plural sample trackings 7 in which plural sample containers are mounted can be set at a sample tracking charging unit 6, and the charged sample trackings are sequentially conveyed to a movable range of a first conveying arm, namely, a sample dispensing position for samples through inner conveying paths 8 and 10. On an extended line of the conveying path 10 in the direction opposed to the conveying direction, provided is an emergency sample charging unit 9 from which emergency sample trackings can be charged in the direction shown by an arrow 10. The reference numeral 16 denotes the sample tracking conveyed to the movable range of the first conveying arm 20, and 17 denotes the plural sample containers containing samples on the sample tracking 16.

After completion of an examination, the sample tracking 16 is accommodated in a sample accommodation unit 19 through conveying paths 11 and 18. It should be noted that the reference numeral 12 denotes a bar-code reader, and various data read from the sample trackings and the sample containers by the bar-code reader 12 are accumulated in the storage unit 5.

The first conveying arm 20 takes out the samples as samples from the sample containers 17 such as test tubes on the sample trackings 16 to be dispensed into plural reaction cells 22 of a pretreatment disk 21. The samples for which a retreatment such as dilution has been completed are dispensed as samples into reaction cells 25 of a reaction disk 24 through a second conveying arm 23, and predetermined reagents are charged for analysis from reagent containers 291 and 292 of first and second reagent disks 281 and 282 into the samples dispensed into the reaction cells 25 of the reaction disk 24 using third and fourth conveying arms 26 and 27. It should be noted that the circumferential rotations and stops of the pretreatment disk 21 and the reaction disk 24 on which the reaction cells 22 and the reaction cells 25 are provided, respectively, are repeated at constant cycles by driving mechanisms (not shown) under the control of the control unit 2, so that the plural reaction cells can be intermittently moved.

The plural reagent containers 291 and 292 containing various reagents to be mixed and reacted with the samples are fixed and arranged on the circumferences of the first and second circular reagent disks 281 and 282. Further, the first and second reagent disks 281 and 282 can be positioned while being rotated in the circumferential direction by driving mechanisms (not shown) configured using motors and rotational shafts under the control of the control unit 2. The sample trackings for which the analysis and examination have been completed are conveyed and accommodated into the sample accommodation unit 19 from the sample dispensing position through the conveying paths 11 and 18 as described above.

In the device shown in FIG. 1, the display unit 3 can display under the control of the control unit 2 various screens such as a pretreatment disk screen, to be described later, for displaying various data such as analysis item setting information and measured results of the samples. Further, the input unit 4 is used by an operator inputting various information such as analysis conditions and maintenance and giving an operation instruction. Further, the storage unit 5 stores, as described above, programs, namely, various CPU control programs including display control, sequence programs used for controlling the respective mechanisms, and data, namely, various information such as analysis items and measured results. It should be noted that an example of data to be stored will be described later using the drawings.

The mechanical units such as the retreatment disk and the reaction disk of the automatic analyzing device main body 1 shown in FIG. 1 are controlled by the control unit 2 on the basis of sequences stored in the storage unit 3 and input instructions from the input unit 4. The storage unit 5 further stores various data of the remaining amounts and states of items necessary to operate the device such as reagents, detergents, diluents, and disposables, and these pieces of information are displayed on the display unit 3 through the control unit 2 periodically or if some are changed.

Subsequently, configuration examples of information display screens of the automatic analyzing device according to the embodiment will be described using FIG. 2 to FIG. 9. As well as display control, these screen displays are controlled by programs of the control unit 2 as described above.

Figure 2:
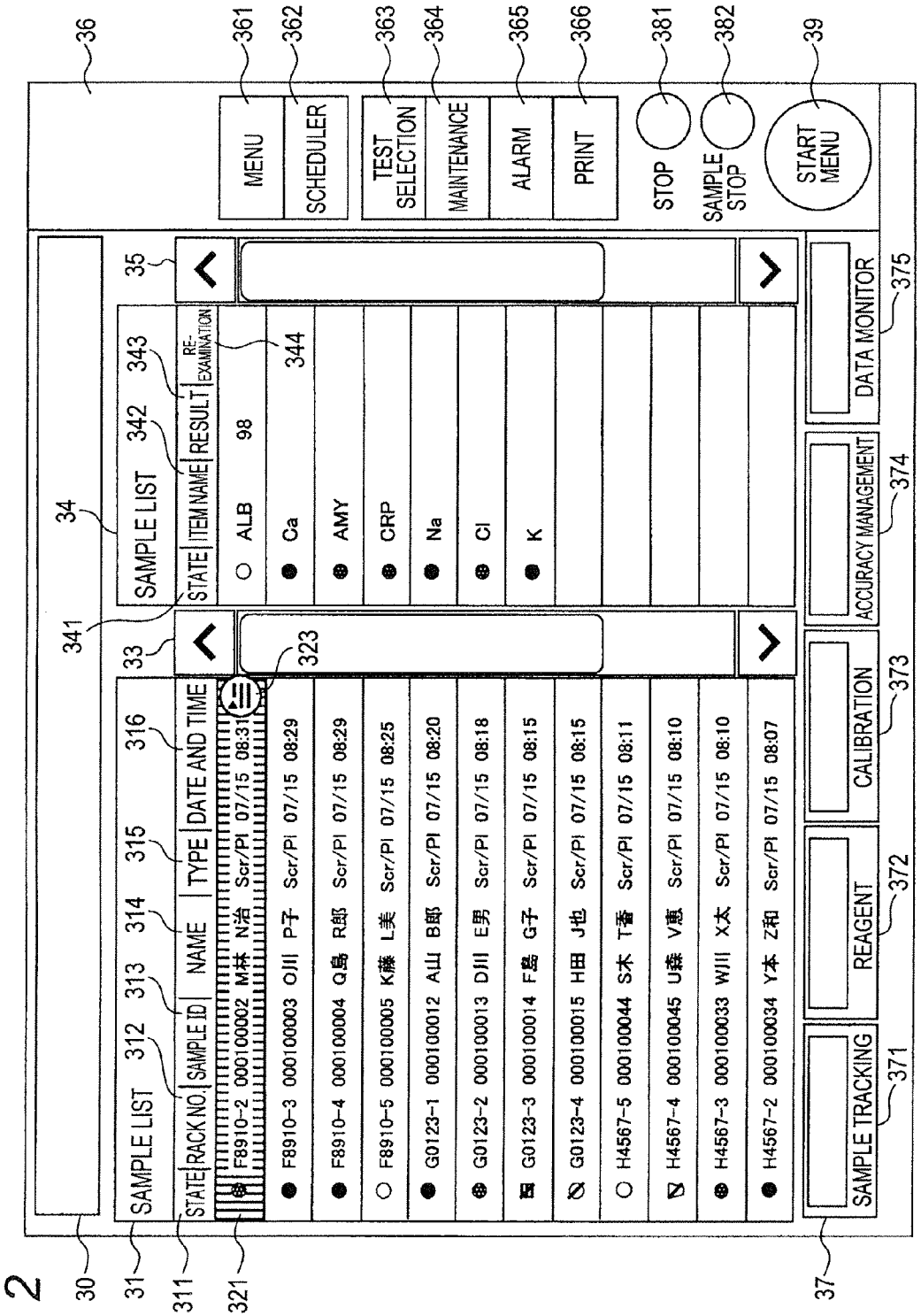
FIG. 2 is a diagram for showing an example of a sample list screen displayed on a display unit of the automatic analyzing device according to the first embodiment.

First, an example of a display screen for a sample list in the embodiment is shown in FIG. 2. On a display screen 30 of the display unit 3, displayed is a sample list area 31 that displays information of the sample trackings. As shown on the top of the sample list 31, displayed are a sample state 311, a rack No. 312, a sample ID 313, a name 314, a type 315, and a date and time 316. The reference numeral 33 denotes a scroll bar used for scrolling data displayed in the sample list display area 31. In FIG. 2, data of the examination result of a highlighted sample 321 that is selected from the sample list display area 31 are displayed in a sample list result display area 34. As shown on the top of the sample list result display area 34, displayed are a state 341, an item name 342, a result 343, and a re-examination 344. The reference numeral 35 denotes a scroll bar. Further, a pop-up button 323 used for displaying a pop-up menu, to be described later, is displayed at the right end of the sample 321 being selected.

Further, in a display area 36, arranged are start buttons such as a menu button 361, a scheduler button 362, a test selection button 363, a maintenance button 364, an alarm button 365, and a print button 366, and buttons such as a stop button 381 and a sample stop button 382. As similar to the above, in a display area 37, arranged are display instruction buttons such as a sample tracking button 371, a reagent button 372, a calibration button 373, an accuracy management button 374, and a data monitor button 375. It should be noted that the reference numeral 39 denotes a start menu button. It is obvious that operation instructions by these various buttons can be realized using ordinary techniques.

Figure 3:
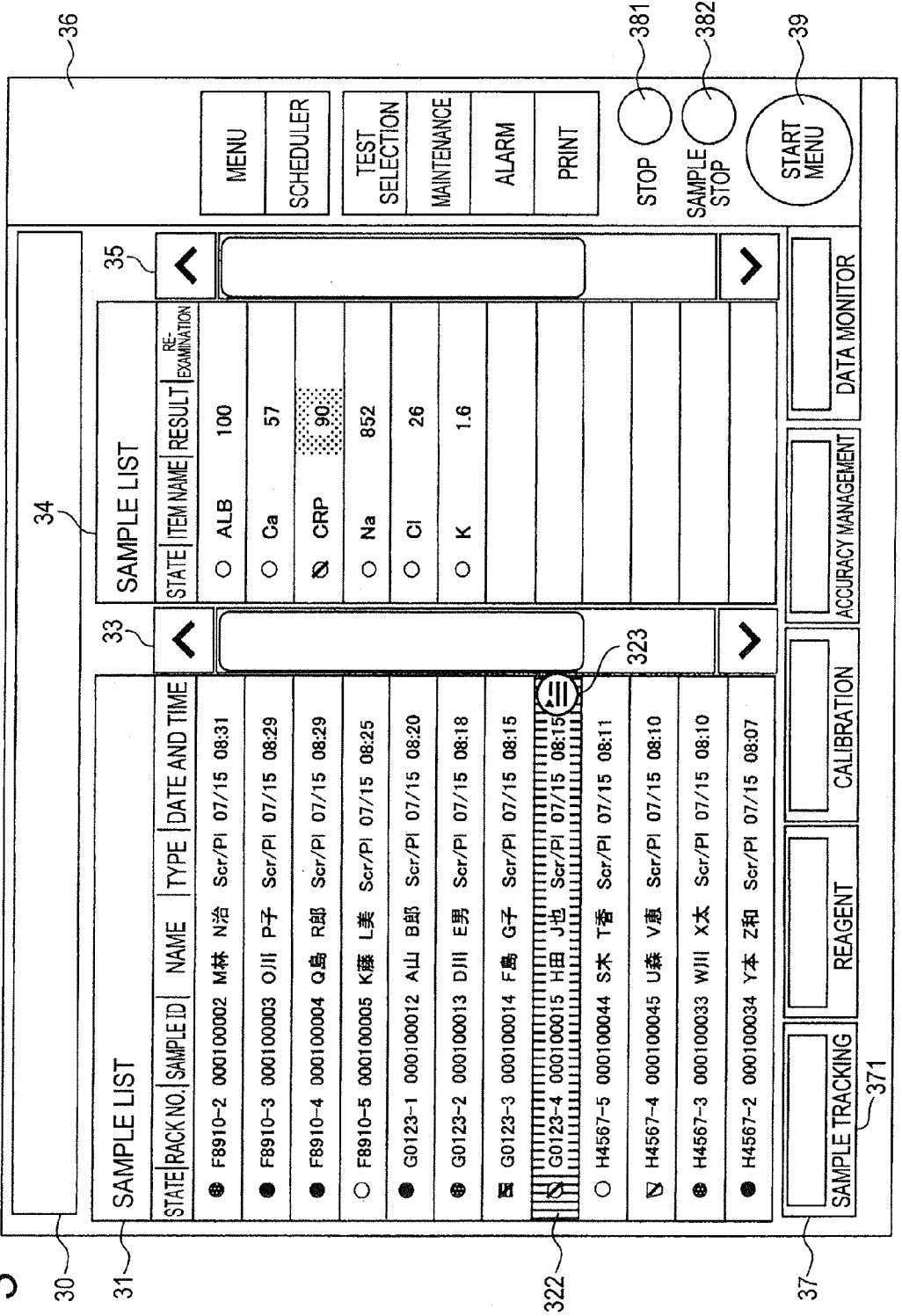
FIG. 3 is a diagram for showing another example of the sample list screen displayed on the display unit of the automatic analyzing device according to the first embodiment.
Figure 4:
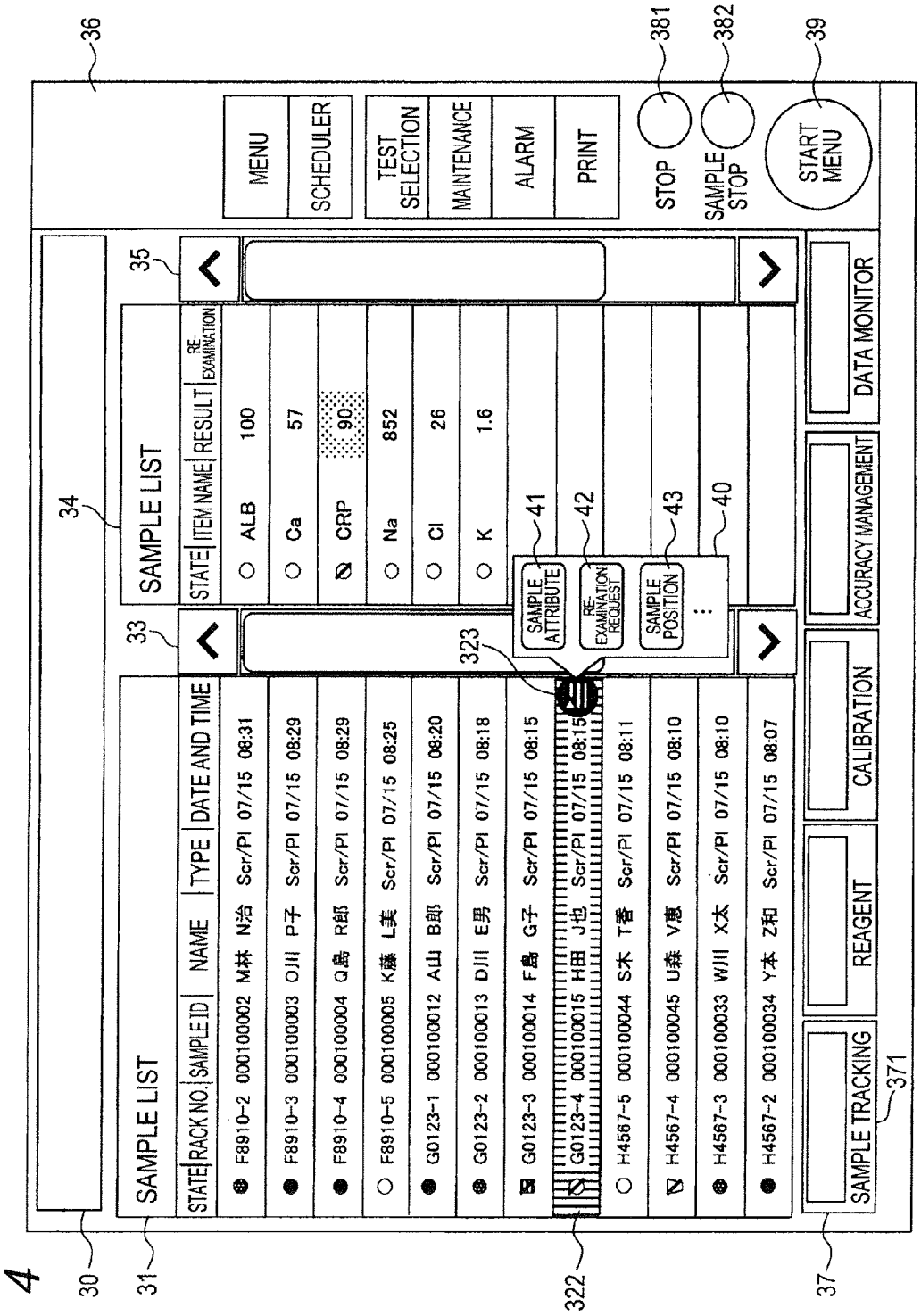
FIG. 4 is a diagram for showing still another example of the sample list screen displayed on the display unit of the automatic analyzing device according to the first embodiment.

Each of FIG. 3 and FIG. 4 shows another example of the sample list display screen as similar to FIG. 2. In each of FIG. 3 and FIG. 4, a sample 322 corresponding to the rack No. G0123-4 and the sample ID 000100015 is selected and highlighted. Then, the data of the examination result are displayed in the sample list result display area 34. Further, as being apparent from each drawing, the figure 90 of C-reactive protein (CRP) is highlighted to show the figure is abnormal.

Further, FIG. 4 shows a case in which a pop-up menu 40 is displayed following a click of the pop-up button 323 displayed for the highlighted sample 322. Near the pop-up button 323 displayed for the sample selected and highlighted in the sample list 31, the pop-up menu is displayed and overlapped as another window showing menu options for the sample. The pop-up menu is displayed as a pop-up window from the pop-up button 323 in the embodiment. In the pop-up menu 40, displayed are menu buttons such as a sample attribute button 41, a re-examination request button 42, and a sample position button 43. If a user selects any one of the buttons, the screen can be moved to a desired process and screen display. For example, with a click of the re-examination request button 42, a screen for a test selection shown in FIG. 9, to be described later, is displayed. The pop-up button 323 shows that there exists a selectable menu for the selected sample and is displayed for each sample in the list. Thus, the operator can smoothly proceed to a step of menu selection while definitely recognizing that the operation is for the selected sample. Further, since the pop-up menu 40 is displayed near the pop-up button 323, a desired menu can be reliably selected with less movement of visual lines. Furthermore, the pop-up button 323 is especially effective in the display unit 3 configured using a touch panel. For a touch panel, it is difficult to have plural functions, when the screen is touched, such as those provided at left and right buttons of a mouse. For example, it is difficult to allocate a function such as "sample selection with a left click and menu display with a right click". Displaying the pop-up button 323 for each sample as in the embodiment allows the operator to easily make a selection in the menu for the sample. Further, displaying the pop-up button 323 at the right end of the selected sample is reminiscent of a right click of a mouse, and the operator can intuitively recognize that the menu is displayed for the selected sample.

Figure 5:
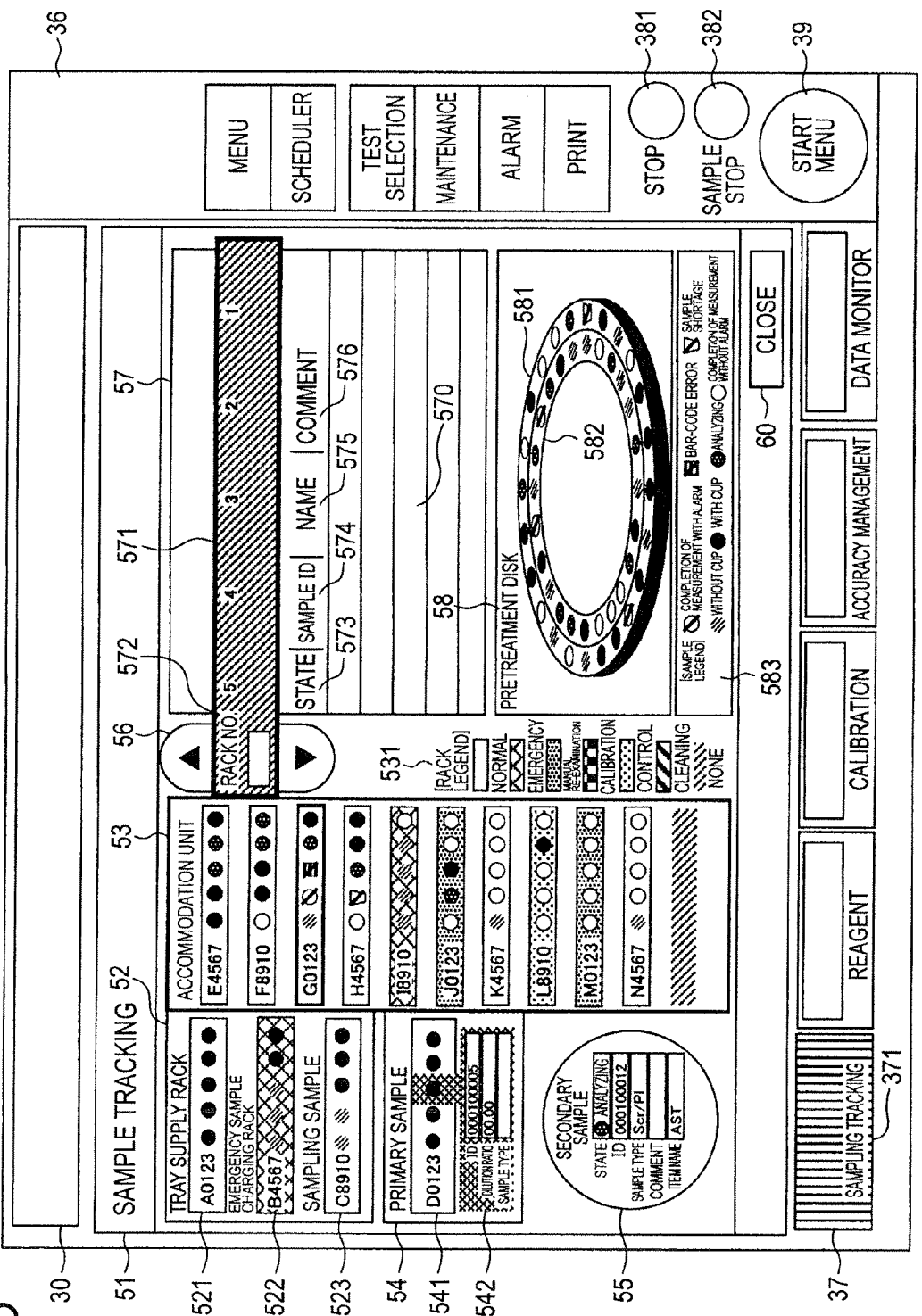
FIG. 5 is a diagram for showing an example of a sample tracking screen displayed on the display unit of the automatic analyzing device according to the first embodiment.

A sample tracking display screen is shown in each of FIG. 5 to FIG. 8 as another example of the information display screen in the embodiment. As shown in FIG. 5, an entire process display area 52 is displayed in the left half of a sample tracking display screen 51 of the embodiment, an enlarged display area 57 is displayed on the upper side of the right half, and a pretreatment disk display area 58 is displayed on the lower side thereof. The sample tracking display screen 51 is displayed when the sample tracking display instruction button 371 in the display area 37 is pressed. When the button of the sample tracking 371 is selected and pressed, the entire process display area 52, the enlarged display area 57, and the pretreatment disk display area 58 are displayed in the sample tracking display area 51 of the display screen 30 of the display unit 3 under the control of the control unit 2.

In the entire process display area 52, displayed are various areas for showing the entire process of the examination such as the positions of the plural sample trackings. Specifically, in the entire process display area 52, displayed are a tray supply rack 521, an emergency sample charging rack 522, a sampling sample 523, an accommodation unit display area 53 for displaying the sample trackings accommodated in the sample accommodation unit 19, a primary sample display area 54, and a secondary sample display area 55. Here, in the secondary sample area 55, displayed are data of a single sample being analyzed. However, data displayed in the other areas are data on a sample tracking basis. The screen display on a sample tracking basis allows the operator to be able to entirely recognize the positions, examination states and the like of the charged sample trackings in the device.

Here, the tray supply rack 521 indicates a sample tracking that is on the conveying paths 8 and 10 after being charged from the sample tracking charging unit 6 but has yet to be conveyed to a movable range of the first conveying arm 20, namely, to the sample dispensing position for the sample. The emergency sample charging rack 522 indicates an emergency sample charging rack charged from the emergency sample charging unit 9. Further, the sampling sample indicates a sample tracking during sample dispensing for pretreatment. The operator can visually recognize the positions and examination states of the respective sample trackings while viewing the display screen of the entire process display area 52 under the display control of the embodiment.

Further, in the entire process display area 52, displayed are the primary sample display area 54 and the secondary sample display area 55 as described above. Here, the primary sample refers to a sample that has been dispensed into the pretreatment disk 21 by the first conveying arm. Further, the secondary sample refers to a sample being analyzed after a pretreated sample in the reaction cell 22 of the pretreatment disk 21 is dispensed into the reaction cell 25 of the reaction disk 24 by the second conveying arm 23. A primary sample tracking 541 and detailed data 542 of a highlighted sample can be displayed in the primary sample display area 54.

It should be noted that a rack legend 531 is displayed on the lower right side of the accommodation unit display area 53 of the sample tracking display area 51, and displayed are rack legend areas in different colors such as "normal", "emergency", "manual re-examination", "calibration", "control", "cleaning", and "none". In the embodiment, the rack legend 531 is displayed to explain the states of information and cannot be selected. However, it is obvious that the rack legend 531 may be selected by pressing buttons. The reference numeral 56 on the upper right side of the accommodation unit display area 53 denotes a scroll bar for scrolling the accommodation unit display area 53. Scrolling the scroll bar 56 can sequentially display in the accommodation unit display area 53 the plural sample trackings accommodated in the sample accommodation unit 19. Then, the detailed information of the sample tracking selected by the operator is displayed in a sample state display area 570 and a sample tracking enlarged display area 571 on the enlarged display area 57. In the sample state display area 570, displayed are a state 573 of each sample, a sample ID 574, a name 575, and a comment 576 in a sample list format. As will be described later using the drawings, a selected sample tracking No. 572 and the states of the samples on the sample tracking are enlarged and displayed in the sample tracking enlarged display area 571 on the basis of a sample legend.

The reference numeral 58 denotes a pretreatment disk display area on the sample tracking display screen 51. In the pretreatment disk display area 58, displayed is a perspective view for showing the states of the samples in the all reaction cells on the pretreatment disk 21 shown in FIG. 1. The reference numerals 581 and 582 denote areas for schematically showing the examination states and the like of the doubly-placed plural reaction cells 22 on the pretreatment disk 21. The states of the samples in the respective reaction cells are shown using a sample legend 583 displayed on the lower side of the pretreatment disk display area 58, and thus the operator who is conducting the examination can easily understand the states of the samples.

As being apparent from FIG. 5, "completion of measurement with alarm", "bar-code error", "sample shortage", "without cup", "with cup", "analyzing", and "completion of measurement without alarm" are displayed in the sample legend 583. In the embodiment, the sample legend 583 is displayed to explain the states of information, and cannot be selected. However, the sample legend 583 may be selected by pressing buttons. The operator can visually and easily confirm the states of the samples in the sample trackings accommodated and displayed in the pretreatment disk display area 58 and the sample accommodation unit display area 53 on the basis of legend symbols using the sample legend 583.

Figure 6:
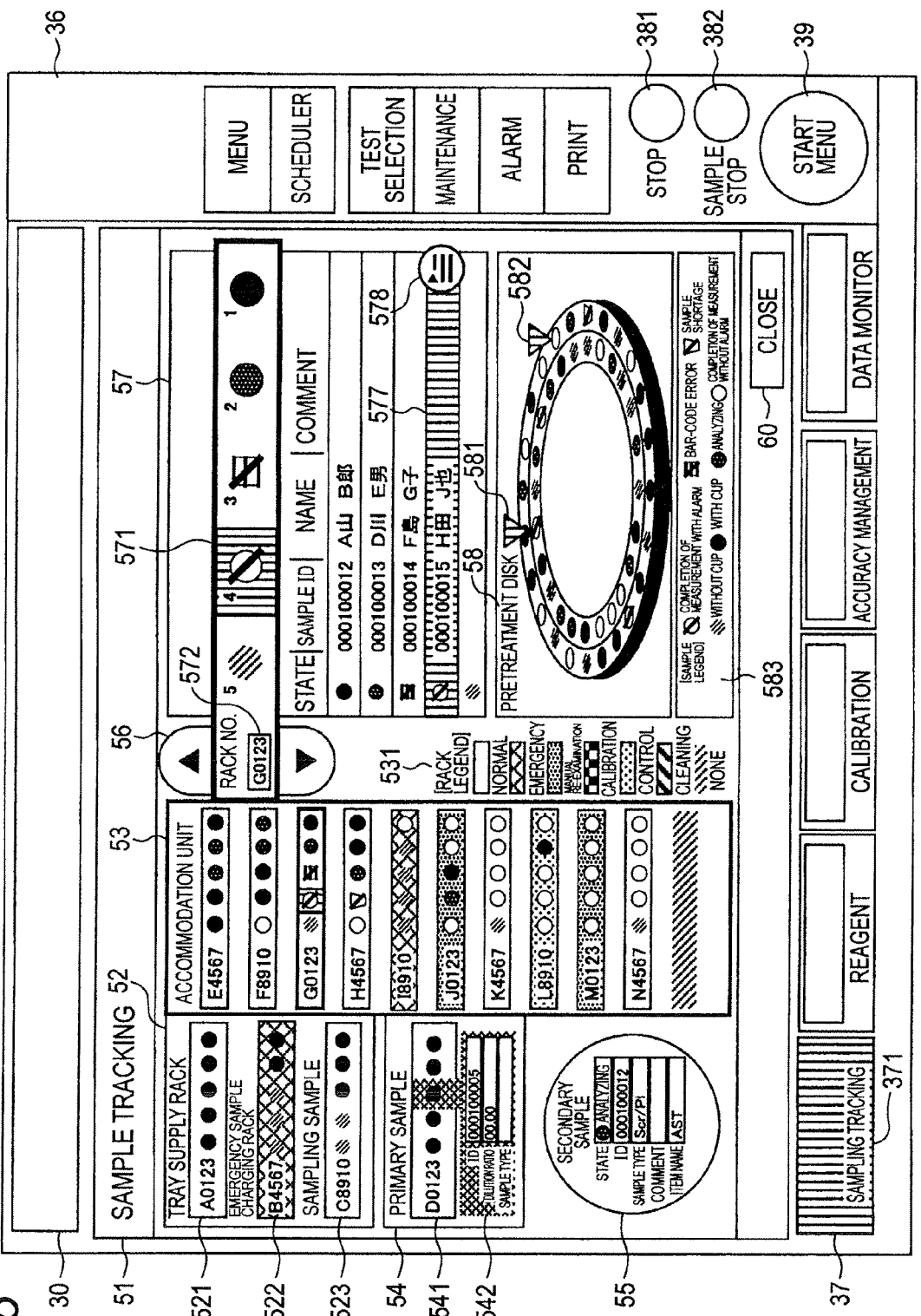
FIG. 6 is a diagram for showing another example of the sample tracking screen displayed on the display unit of the automatic analyzing device according to the first embodiment.

Next, FIG. 6 shows an example of a display screen after the operator selects a sample tracking G0123 displayed in the accommodation unit display area 53 shown in FIG. 5. In the accommodation unit display area 53, the selected sample tracking G0123 is displayed with a thick outer frame. Further, the selected sample tracking G0123 is displayed in the rack No. display area 572, and the examination states of five samples on the sample tracking G0123 are displayed in the sample tracking enlarged display area 571 on the basis of the above-described sample legend 583. A sample 4 in the sample tracking G0123 is in a state of "completion of measurement with alarm" as shown in FIG. 6.

If the operator selects a sample display area 577 corresponding to the sample 4 in this state, the sample display area 577 is highlighted and a pop-up menu button 578 is displayed. Further, arrow marks 581 and 582 are displayed in the pretreatment disk display area 58 to indicate the reaction cells of the pretreatment disk 21 in which the corresponding samples exist. Displaying the arrow marks 581 and 582 allows the operator to be able to visually determine whether or not the samples required to have a re-examination exist on the pretreatment disk 21 and to recognize the positions of the samples existing on the pretreatment disk 21. Thus, the operator can visually determine the necessity of a manual re-examination to be described later.

Figure 7:
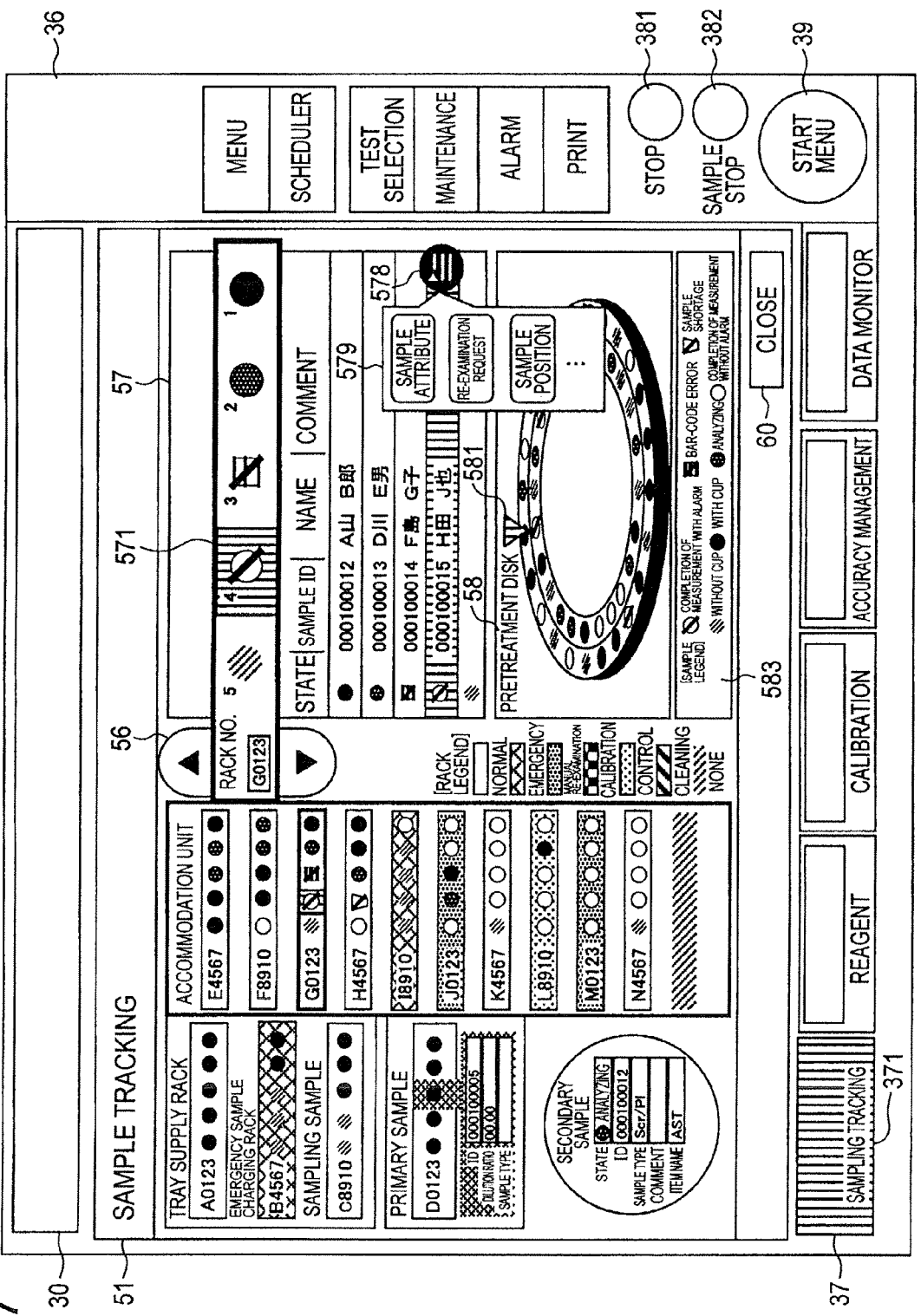
FIG. 7 is a diagram for showing still another example of the sample tracking screen displayed on the display unit of the automatic analyzing device according to the first embodiment.

FIG. 7 shows a state in which a pop-up menu 579 is displayed on the screen by the operator pressing the pop-up menu button 578 to confirm detailed content of data and to perform further processes for the sample ID 000100015 that is indicated as "completion of measurement with alarm" in the sample legend. As similar to the pop-up menu 40 in FIG. 4, the pop-up menu 579 is also displayed and overlapped near the pop-up button 578 for the sample selected and highlighted in the sample display area 577 as another window showing menu options for the sample.

Figure 8:
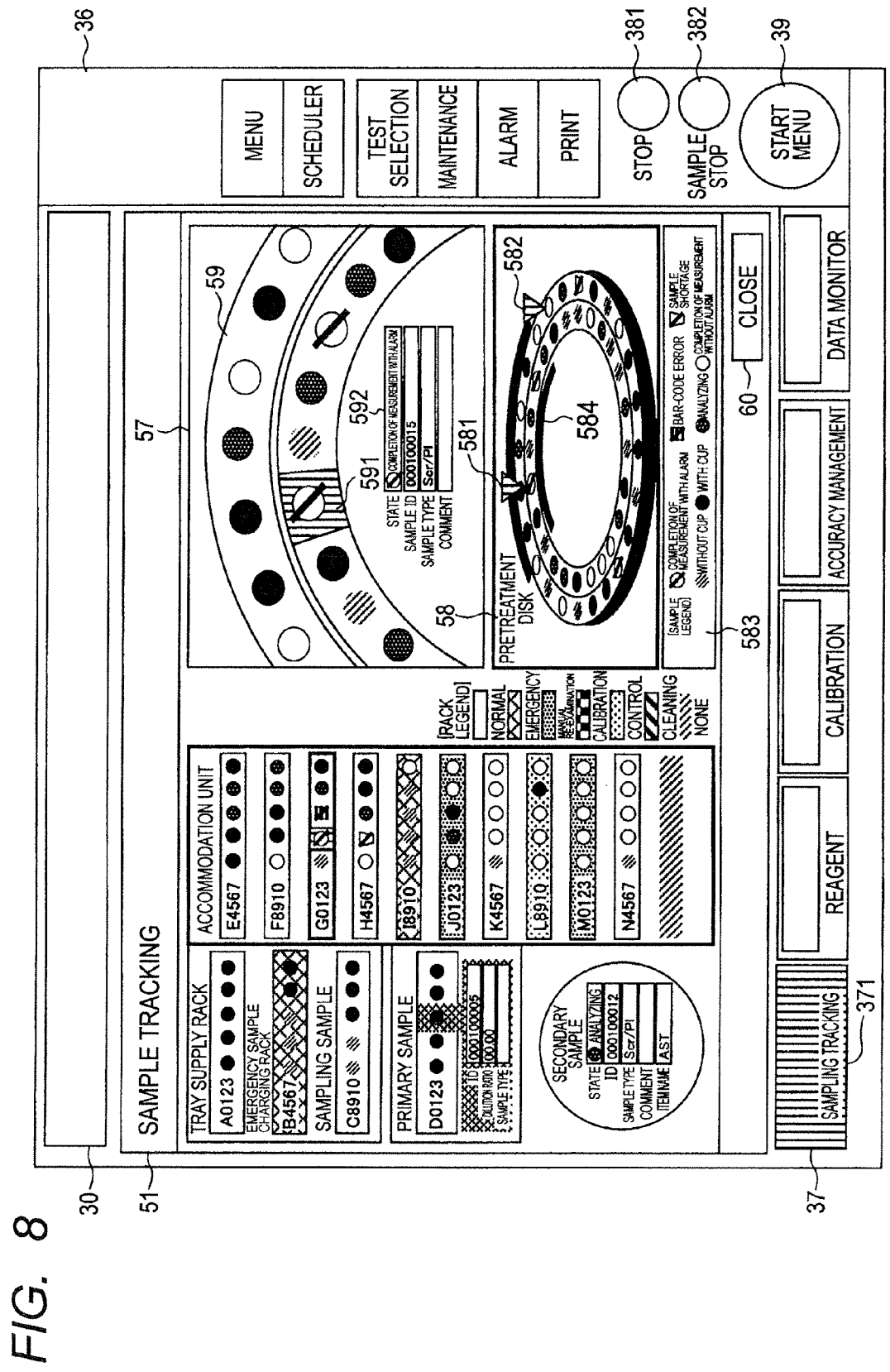
FIG. 8 is a diagram for showing still another example of the sample tracking screen displayed on the display unit of the automatic analyzing device according to the first embodiment.

If the operator selects "sample attribute", a pretreatment disk enlarged screen 59 functioning as a pretreatment disk enlarged display area is displayed in the enlarged display area 57 as shown in FIG. 8, instead of the scroll bar 56, the sample tracking enlarged display area 571, and the like displayed in FIG. 7. Specifically, a sample legend group of the samples located at a fan-shaped selection area 584 of the pretreatment disk display area 58 is displayed on the pretreatment disk enlarged screen 59 of the enlarged display area 57, and a sample legend 591 with "completion of measurement with alarm" is highlighted. Further, the sample ID of the sample, the sample type and the like are displayed in an attribute display area 592. The screen display allows the operator to be able to visually obtain the location of the focused sample on the pretreatment disk 21 and the detailed information of the examination states of the sample.

Figure 9:
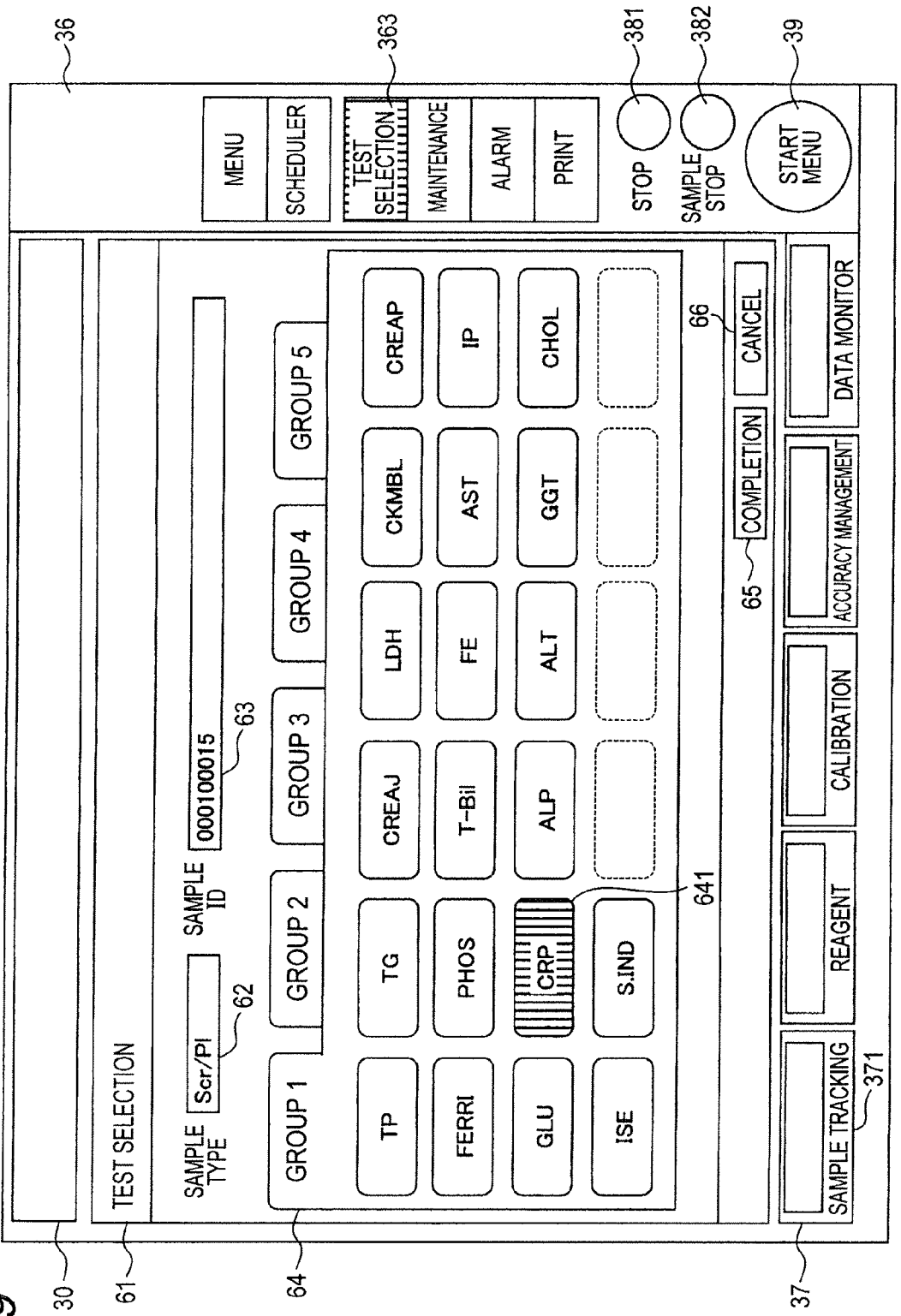
FIG. 9 is a diagram for showing an example of a test selection screen displayed on the display unit of the automatic analyzing device according to the first embodiment.

Next, an example of a test selection display screen is shown in FIG. 9 as another example of the information display screen in the display unit 3 in the embodiment. A test selection display screen 61 displayed on the display screen 30 of the display unit 3 displays a sample type 62, a sample ID 63, and an examination item group 64 of a target sample. If the operator selects CRP 641 as an examination item in the examination item group 64, CRP 641 is being selected and highlighted. It should be noted that the test selection screen display can be displayed by selecting the test selection button 363 of the display area 36. However, the test selection screen display can be also displayed when a re-examination request for a sample is made by selecting "re-examination request" in the pop-up menu 40 of FIG. 4 or the pop-up menu 579 of FIG. 7 as described above. It should be noted that the reference numerals 65 and 66 denote a completion button and a cancel button, respectively, in the drawing.

In the embodiment, the automatic analysis for the samples is executed under the control of the control unit 2 using the above-described device configurations and display screens. Hereinafter, an automatic analyzing operation flow of the embodiment will be sequentially described using flowcharts shown in FIGS. 10 to 12. It should be noted that the flowcharts to be described below are executed on the CPU configuring the above-described control unit 2, and thus each step of the flowcharts is operated in principle mainly by the control unit 2 of the device. However, it is obvious that each step of the flowcharts may be operated mainly by an instruction input by the operator via the input unit 3 or a GUI.

Figure 10:
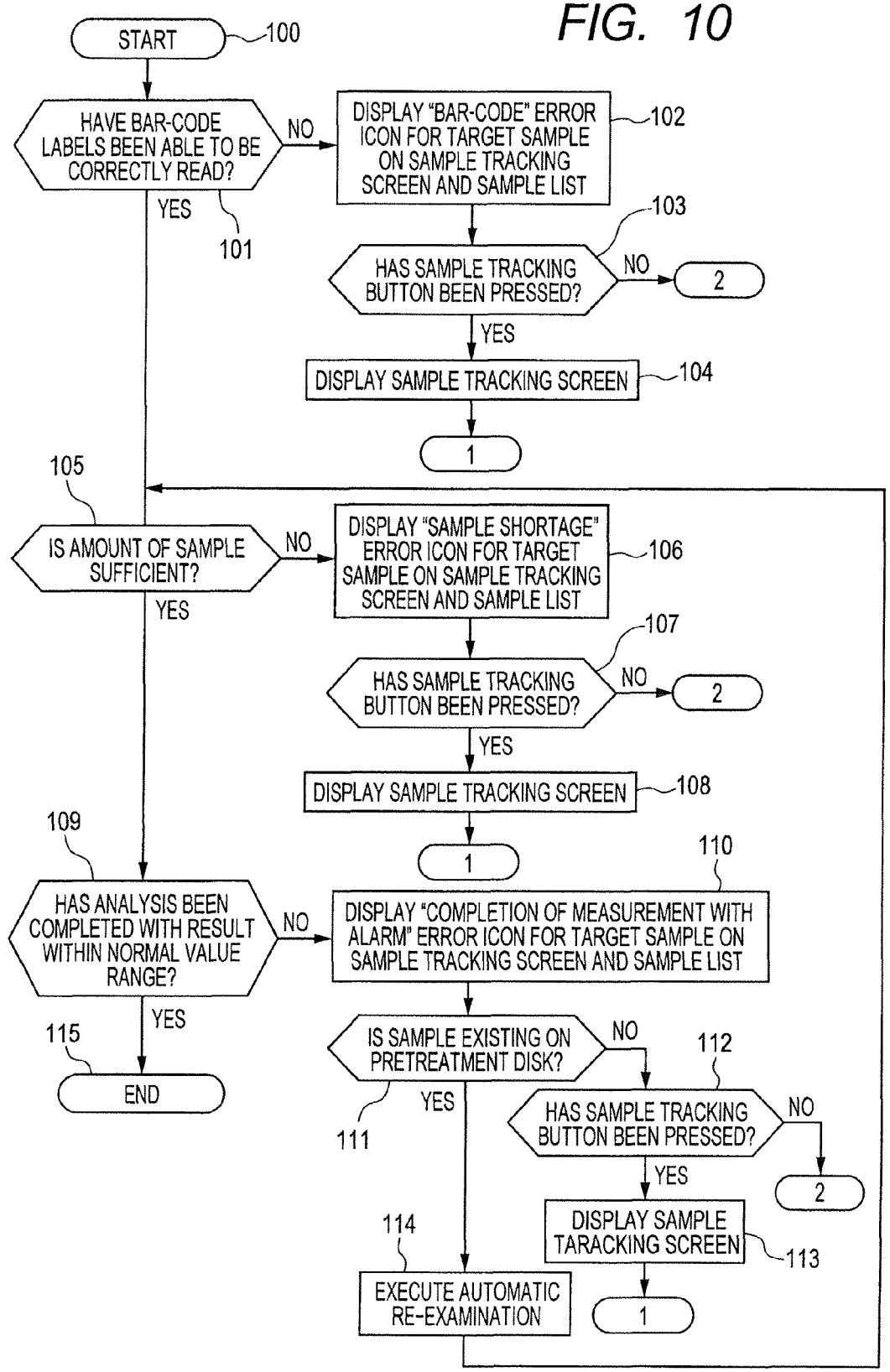
FIG. 10 is a diagram for showing an example of an operation flow of processes performed by the automatic analyzing device according to the first embodiment.

FIG. 10 shows the entire flow of operations from the start of the analysis to the end of the analysis. When the analysis starts (100), it is determined whether or not the bar-code labels of the samples on the sample tracking conveyed on the conveying path 11 have been able to be correctly read by the bar-code reader 12 (101). If the labels have not been able to be correctly read, it is controlled to display a "bar-code" error icon for the target sample on the sample tracking screen 51 and the sample list screen 31. Then, if the sample tracking button 371 of the display area 37 is pressed (YES in 103), the sample tracking screen shown in FIG. 5 and the like is displayed (104). It should be noted that processing flows shown by circles 1 and circles 2 in the drawing will be described later using FIG. 11 and FIG. 12.

If the bar-code labels have been able to be correctly read, it is determined whether or not the amount of samples is sufficient (105). If the amount is insufficient (NO in 105), it is controlled to display a "sample shortage" error icon for the target sample on the sample tracking screen 51 and the sample list screen 31. Thereafter, if the sample tracking button 371 is pressed (YES in 107), the sample tracking screen is displayed as similar to the above (108).

If the amount of samples is sufficient, it is determined whether or not the analysis has been completed with a result within a normal value range (109). If not (NO in 109), a "completion of measurement with alarm" icon is displayed for the target sample on the sample tracking screen 51 and the sample list screen 31 (110). Subsequently, it is determined whether or not the target sample is existing on the pretreatment disk (111). If not target sample is existing on the pretreatment disk (NO in 111), it is determined whether or not the sample tracking button 371 has been pressed (112). If the sample tracking button 371 has been pressed, the sample tracking screen 51 is displayed (113). On the other hand, if the target sample is existing on the pretreatment disk (YES in 111), the automatic re-examination is executed (114). In addition, if the analysis has been completed with a result within a normal value range (YES in 109), the analysis is completed.

Figure 11:
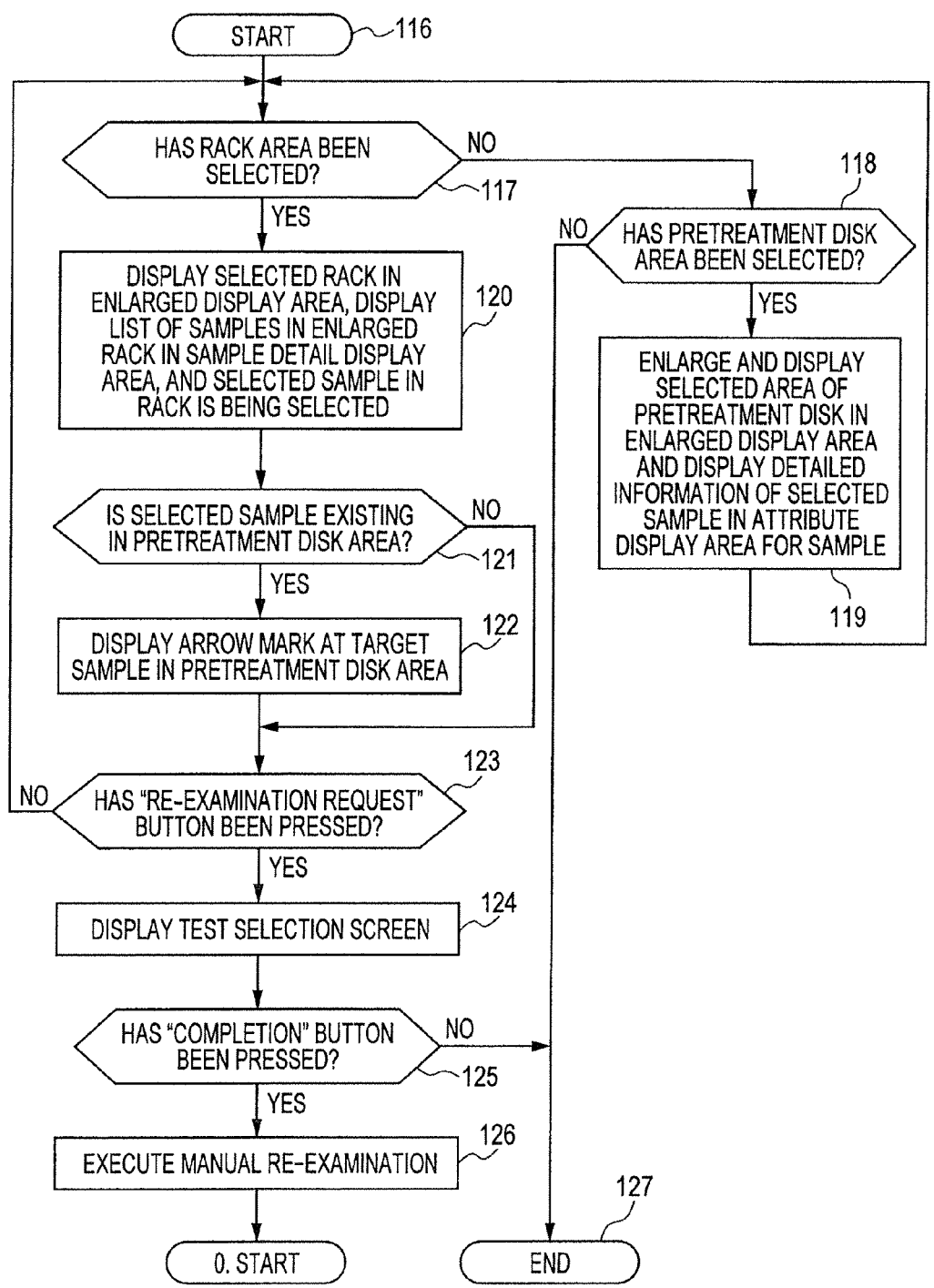
FIG. 11 is a diagram for showing another operation flow of processes performed by the automatic analyzing device according to the first embodiment.

Next, with the use of the processing flow of FIG. 11, there will be described a case in which the processes shown by the circles 1 of FIG. 10 are executed on the sample tracking screen 51 by the operator. When the sample tracking screen 51 is displayed to start a confirmation process (116), it is first determined whether or not the sample tracking of the rack display area in the entire process display area 52 has been selected (117). If no sample tracking of the rack display area has been selected (NO in 117), it is determined whether or not the pretreatment disk area 58 has been selected (118). If not, the process is completed (127). If the pretreatment disk area 58 has been selected (YES in 118), a selection area for the pretreatment disk enlarged screen 59 is displayed in the enlarged display area 57, and detailed attribute information of the selected sample is displayed in the attribute display area 593 for the sample. Further, when any one of the sample trackings in the entire process display area 52 has been selected (YES in 117), the selected sample tracking is displayed in the enlarged display area 57, a list of the samples in the enlarged rack is displayed in the sample tracking enlarged display area 571, the states of the samples in the rack are displayed in the sample state display area 570, and the sample selected in the sample tracking is highlighted (120). Subsequently, it is determined by the control unit 3 whether or not the selected sample is existing on the pretreatment disk 21 (121). If existing, (YES in 121), the control unit 3 displays the arrow mark 581 or 582 for the corresponding sample in the pretreatment disk display area 58 (122). Further, if the selected sample is existing on the pretreatment disk 21, the control unit 3 executes the automatic re-examination for the sample under the control of a preliminarily-set program. The examination item of the automatic re-examination is set as, for example, an examination item with alarm.

As described above, the operator can recognize the arrow mark 581 or 582 by viewing the pretreatment disk display area 58 of the sample tracking display area 51. Thus, if the corresponding sample is existing on the pretreatment disk 21, the operator can recognize the automatic re-examination to be executed. Even if the arrow mark 581 or 582, or the like is not displayed and if the operator requests for the re-examination of the corresponding sample, the pop-up menu 579 is displayed by pressing the pop-up menu button 578, and the re-examination request is selected and pressed. If the control unit 3 detects that the operator has pressed the "re-examination request" button (YES in 123), the test selection screen shown in FIG. 9 is displayed on the display unit 3.

Further, the operator selects, for example, CRP 641 as an examination item for the target sample on the test selection screen 61, presses the test selection button 363, and completes the test selection with the completion button 65. If the control unit 3 detects that the operator has pressed the "completion" button (YES in 125), a manual re-examination is executed. It should be noted that the manual re-examination is started by the operator charging the sample tracking mounting the sample as the re-examination targets to the sample tracking charging unit 6, unlike the automatic re-examination, as described above, in which the control unit 2 of the device performs a re-examination for the sample on the pretreatment disk 21 in accordance with the preliminarily-set program procedures.

Figure 12:
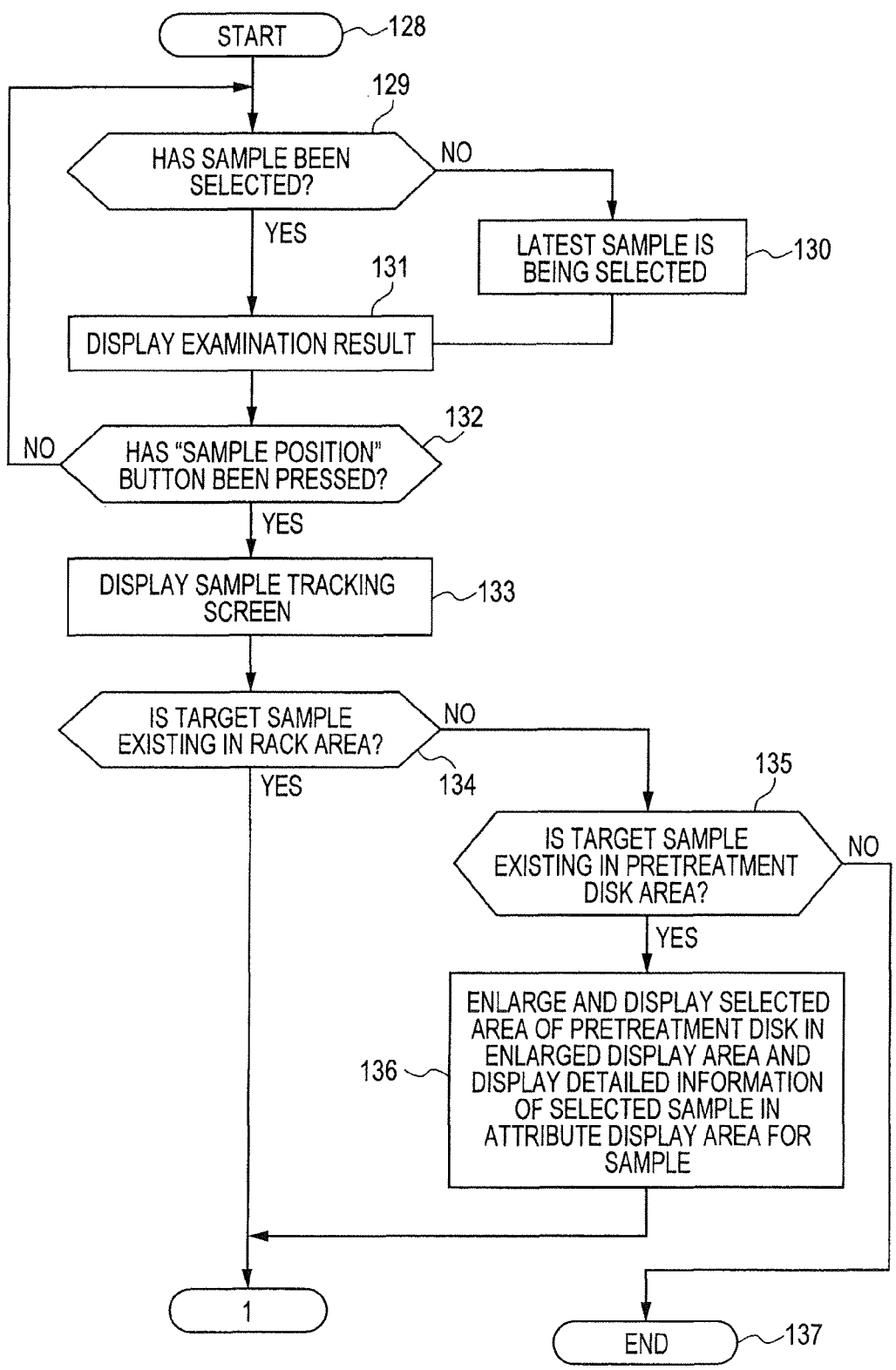
FIG. 12 is a diagram for showing still another operation flow of processes performed by the automatic analyzing device according to the first embodiment.

Further, on the basis of the processing flow of FIG. 12, there will be described a case in which the processes shown by the circles 2 of FIG. 10 are executed on the sample list screen 31 by the operator. When the sample list screen 31 is displayed to start a confirmation process (128), it is first determined whether or not the sample on the sample list screen 31 has been selected (129). If no sample has been selected (NO in 129), the latest sample is being selected (130). If the sample has been selected (YES in 129), the examination result is displayed in the sample list result display area 34. Subsequently, it is detected by the control unit 3 whether or not the pop-up menu button 323 has been pressed and the sample position button 43 has been selected by the operator. If the "sample position" button 43 has been pressed (YES in 132), the sample tracking screen 51 is displayed (133). At the same time, it is determined whether or not the target sample is existing in the rack display area of the entire process display area 52 (134). If the target sample is existing (YES in 134), the process moves to the above-described processing flow of FIG. 11. If no target sample is existing (NO in 134), it is determined whether or not the target sample is existing on the pretreatment disk 21 (135). If existing (YES in 135), the pretreatment disk enlarged screen 59 is displayed in the enlarged display area 57, and the selected sample 591 is highlighted. At the same time, the detailed information of the selected sample is displayed in the attribute display area 592 for the sample (136). Then, the process moves to the processing flow of FIG. 11. It should be noted that if no target sample is existing on the pretreatment disk 21, the process is completed (137).

FIG. 13 shows an example of a table for various data of each sample tracking accumulated in the storage unit 5 of the automatic analyzing device in the embodiment. In the drawing, the reference numerals 1380, 1381, 1382, 1383, 1384, 1385, 1386, 1387, 1388, and 1389 in the horizontal axis of a table 138 represent a rack No., a rack type, a rack position, a position, a sample ID, a rack position state, an examination item, a result, a pretreatment disk position, and a pretreatment disk state, respectively.

The preferred embodiment of the present invention has been described as the first embodiment. It is obvious that the present invention is not limited to the configuration of the first embodiment.

As a characteristic of the embodiment, provided is an automatic analyzing device that analyzes samples, the device including: a pretreatment disk into which samples on sample trackings charged from a charging unit and conveyed through conveying paths are dispensed; a reaction disk into which the samples pretreated at the pretreatment disk are dispensed; a control unit that controls operations of the pretreatment disk and the reaction disk; a display unit that is controlled by the control unit; and a storage unit that stores data related to the samples, wherein the control unit controls to display on a display screen of the display unit an entire process display area for showing the states of the plural sample trackings in the entire process, and a pretreatment disk display area for showing the states of the samples on the pretreatment disk.

Further, as another characteristic of the embodiment, provided is an automatic analyzing method for an automatic analyzing device that analyzes samples and includes a control unit and a display unit, wherein when the control unit displays on the display unit the states of the samples processed at a pretreatment disk into which the samples on sample trackings conveyed through conveying paths are dispensed and at a reaction disk into which the pretreated samples are dispensed, the control unit controls to display on a display screen of the display unit an entire process display area for showing the states of the sample trackings in the entire process, and a pretreatment disk display area for showing the states of the samples on the pretreatment disk.

Moreover, the above-described embodiment has further the following characteristics.

The control unit controls to display on the display screen of the display unit a sample tracking enlarged display area for enlarging the sample tracking selected among the plural sample trackings displayed in the entire process display area.

The control unit controls to display information of a primary sample and a secondary sample in the entire process display area.

The control unit controls to display a pretreatment disk enlarged display area for enlarging the states of the samples displayed in the pretreatment disk display area.

The control unit controls to display in the entire process display area a tray supply rack, an emergency sample charging rack, a sampling sample, and the primary sample on a rack basis.

The control unit displays in the entire process display area the secondary sample on a sample basis. Further, the control unit controls to display in the pretreatment disk display area an arrow mark indicating the position of the sample selected among the plural samples in the sample tracking displayed in the sample tracking enlarged display area.

If the sample selected from the plural samples in the sample tracking displayed in the sample tracking enlarged display area is existing on the pretreatment disk, the control unit controls to execute a re-examination of the selected sample using the sample existing on the pretreatment disk.

If the sample selected from the plural samples in the sample tracking displayed in the sample tracking enlarged display area is not existing on the pretreatment disk, the control unit monitors whether or not a re-examination request for the selected sample is input.

According to the above-described embodiment, an operator can visually recognize the position states of the sample trackings in the entire process in the automatic analyzing device having the pretreatment disk. Further, if the sample in the sample tracking needs to be re-examined, it is possible to recognize on the pretreatment disk display screen whether or not the sample is existing on the pretreatment disk. Thus, the manual re-examination request can be smoothly made.

INDUSTRIAL APPLICABILITY

The present invention is useful in an automatic analyzing device that conducts a qualitative/quantitative analysis for biological samples, and is especially useful as a user interface of an automatic analyzing device having a display screen.

REFERENCE SIGNS LIST

1 . . . automatic analyzing device main body
2 . . . control unit
3 . . . display unit
4 . . . input unit
5 . . . storage unit
6 . . . sample tracking charging unit
7 . . . sample tracking
8 . . . conveying path
9 . . . emergency sample charging unit
10 . . . conveying path
11 . . . conveying path
12 . . . bar-code reader
16 . . . sample tracking
17 . . . sample container
18 . . . conveying path
19 . . . sample accommodation unit
20, 23, 26, 27 . . . conveying arm
21 . . . pretreatment disk
22 . . . reaction cell
24 . . . reaction disk
25 . . . reaction cell
281, 282 . . . reagent disk
291, 292 . . . reagent container
30 . . . display screen
31 . . . sample list display area
321, 322 . . . sample of sample list
33, 35, 56 . . . scroll bar
34 . . . sample list result display area
36, 37 . . . button display area
381, 382 . . . stop button
39 . . . start menu button
40 . . . pop-up menu
51 . . . sample tracking display area
52 . . . entire process display area
53 . . . accommodation unit display area
54 . . . primary sample display area
55 . . . secondary sample display area
57 . . . enlarged display area
570 . . . sample state display area
571 . . . sample tracking enlarged display area
572 . . . rack No.
573 . . . state
574 . . . sample ID
575 . . . name
576 . . . comment
577 . . . sample display area
58 . . . pretreatment disk display area
59 . . . pretreatment disk enlarged screen
60 . . . close button
61 . . . test selection display area
62 . . . sample type display area
63 . . . sample ID display area
64 . . . sample item group
65 . . . completion button
66 . . . cancel button

The invention claimed is:

1. An automatic analyzing device that analyzes samples, the automatic analyzing device comprising:
a processor;
a display unit connected to the processor; and
one or more storage media connected to the processor, the storage media storing instructions that, when executed by the processor, causes the processor to control analyzing operations, control the display unit, and to store data related to the samples in the storage media,
wherein the storage media further store instructions that, when executed by the processor, causes the processor to:
display a first sample list containing respective sample IDs and analysis states of the samples as display items on a first display screen of the display unit in a selectable manner,
display, when one of the samples in the first sample list is selected and there exists a selectable processing menu for the selected sample, a first pop-up button for displaying the selectable processing menu for the selected sample in a display items area of the selected sample on the first display screen, and
display, when the first pop-up button is pressed, a plurality of options of the selectable processing menu for the selected sample in a selectable manner adjacent the first pop-up button as a plurality menu buttons on the first display screen,
switch to display, when one of the menu buttons adjacent the first pop-up button is selected on the first display screen, a second sample list containing the sample IDs and the analysis states of the samples and the selected sample which are on a same rack in an enlarged display area on a second display screen of the display unit in a selectable manner,
display, when one of the samples in the second sample list is selected and there exists the selectable processing menu for the selected sample, a second pop-up button for the selectable processing menu for the selected sample in a sample display area of the selected sample, and a mark indicating a location of the selected sample on a pretreatment disk in a pretreatment disk display area on the second display screen,
display, when the second pop-up button is pressed, a plurality of options of the selectable processing menu for the selected sample in a selectable manner adjacent the second pop-up button as a plurality menu buttons on the second display screen, and
switch to display, when one of the menu buttons adjacent the second pop-up button is selected on the second display screen, an enlarged area of the location of the selected sample on the pretreatment disk and the analysis state of the selected sample in the enlarged display area on the second display screen of the display unit.

2. The automatic analyzing device according to claim 1, wherein the storage media further store instructions that, when executed by the processor, causes the processor to:
highlight the selected sample in the first sample list, display the first pop-up button at an end of the display items area of the selected sample, and overlap and display the menu buttons as a different window adjacent the pop-up button.

3. The automatic analyzing device according to claim 1, wherein the storage media further store instructions that, when executed by the processor, causes the processor to:
display on the second display screen of the display unit an entire process display area including the analysis states of the samples held on the plurality of racks.

4. The automatic analyzing device according to claim 3, wherein the storage media further store instructions that, when executed by the processor, causes the processor to:
display information of a primary sample and a secondary sample of the samples in the entire process display area.

5. The automatic analyzing device according to claim 4, wherein the storage media further store instructions that, when executed by the processor, causes the processor to:
display in the entire process display area a tray supply rack, an emergency sample charging rack, a sampling sample, and the primary sample on a rack basis.

6. The automatic analyzing device according to claim 4, wherein the storage media further store instructions that, when executed by the processor, causes the processor to:
display in the entire process display area the secondary sample on a sample basis.

7. The automatic analyzing device according to claim 1, wherein, when there does not exist the selectable processing menu for the selected sample, the pop-up button and the menu buttons are not displayed.

8. The automatic analyzing device according to claim 1, wherein, when there exists the selectable processing menu for the selected sample, the menu buttons, corresponding to the selectable processing menu for the selected sample, are extracted from a set of the options.

9. An information display method for an automatic analyzing device that analyzes samples, the information display method comprising:
displaying a first sample list containing respective sample IDs and analysis states of the samples as display items in a selectable manner on a first display screen of a display unit controlled by a processor;
upon selecting one of the samples in the first sample list and when there exists a selectable processing menu for the selected sample, displaying a first pop-up button for displaying the selectable processing menu for the selected sample in a display items area of the selected sample on the first display screen;
upon selecting the first pop-up button, displaying a plurality of options of the selectable processing menu for the selected sample in a selectable manner adjacent the first pop-up button as a plurality of menu buttons on the first display screen;
upon selecting one of the menu buttons adjacent the first pop-up button on the first display screen, switching to display a second sample list containing the sample IDs and the analysis states of the samples and the selected sample which are on a same rack in an enlarged display area on a second display screen of the display unit in a selectable manner,
upon selecting one of the samples in the second sample list and there exists the selectable processing menu for the selected sample, displaying a second pop-up button for the selectable processing menu for the selected sample in a sample display area of the selected sample, and a mark indicating a location of the selected sample on a pretreatment disk in a pretreatment disk display area on the second display screen,
upon selecting the second pop-up button, displaying a plurality of options of the selectable processing menu for the selected sample in a selectable manner adjacent the second pop-up button as a plurality menu buttons on the second display screen, and
upon selecting one of the menu buttons adjacent the second pop-up button is selected on the second display screen, switching to display an enlarged area of the location of the selected sample on the pretreatment disk and the analysis state of the selected sample in the enlarged display area on the second display screen of the display unit.

10. The information display method for an automatic analyzing device according to claim 9, further comprising:
highlighting the selected sample in the first sample list, displaying the first pop-up button at an end of the display items area of the selected sample, and overlapping and displaying the menu buttons as a different window adjacent the pop-up button.

11. The information display method for an automatic analyzing device according to claim 9, further comprising:
displaying on the second display screen of the display unit an entire process display area including the analysis states of the samples held on the plurality of racks.

12. The information display method for an automatic analyzing device according to claim 11, further comprising:
displaying on the second display screen information of a primary sample and a secondary sample of the samples in the entire process display area.

13. An automatic analyzing device that analyzes samples, the device comprising:
a pretreatment disk into which samples on sample trackings charged from a charging unit and conveyed through conveying paths are dispensed;
a reaction disk into which the samples pretreated at the pretreatment disk are dispensed;
a processor;
a display unit connected to the processor; and
one or more storage media connected to the processor, the storage media storing instructions that, when executed by the processor, causes the processor to control analyzing operations, the pretreatment disk, the charging unit, the reaction disk, and the display unit, and to store data related to the samples in the storage media,
wherein the storage media further store instructions that, when executed by the processor, causes the processor to:
display a first sample list containing respective sample IDs and analysis states of the samples as display items on a first display screen of the display unit in a selectable manner,
display, when one of the samples in the first sample list is selected and there exists a selectable processing menu for the selected sample, a first pop-up button for displaying the selectable processing menu for the selected sample in a display items area of the selected sample on the first display screen, and
display, when the first pop-up button is pressed, a plurality of options of the selectable processing menu for the selected sample in a selectable manner adjacent the first pop-up button as a plurality menu buttons on the first display screen,
switch to display, when one of the menu buttons adjacent the first pop-up button is selected on the first display screen, a second sample list containing the sample IDs and the analysis states of the samples and the selected sample which are on a same rack in an enlarged display area on a second display screen of the display unit in a selectable manner, and a plurality of locations of a plurality of racks, including the same rack, holding the samples in an entire process display area adjacent to the enlarged display area on the second display screen,
select one of the racks other than the same rack from the entire process display area using a scroll bar,
switch to display the second sample list as containing the sample IDs and the analysis states of the samples on the selected rack,
display, when one of the samples in the second sample list is selected and there exists the selectable processing menu for the selected sample, a second pop-up button for the selectable processing menu for the selected sample in a sample display area of the selected sample, and a mark indicating a location of the selected sample on a pretreatment disk in a pretreatment disk display area on the second display screen, display, when the second pop-up button is pressed, a plurality of options of the selectable processing menu for the selected sample in a selectable manner adjacent the second pop-up button as a plurality menu buttons on the second display screen, and switch to display, when one of the menu buttons adjacent the second pop-up button is selected on the second display screen, an enlarged area of the location of the selected sample on the pretreatment disk and the analysis state of the selected sample in the enlarged display area on the second display screen of the display unit.

14. An information display method for an automatic analyzing device that analyzes samples, the information display method comprising:

displaying a first sample list containing respective sample IDs and analysis states of the samples as display items on a first display screen of the display unit in a selectable manner, displaying, when one of the samples in the first sample list is selected and there exists a selectable processing menu for the selected sample, a first pop-up button for displaying the selectable processing menu for the selected sample in a display items area of the selected sample on the first display screen, and displaying, when the first pop-up button is pressed, a plurality of options of the selectable processing menu for the selected sample in a selectable manner adjacent the first pop-up button as a plurality menu buttons on the first display screen, switching to display, when one of the menu buttons adjacent the first pop-up button is selected on the first display screen, a second sample list containing the sample IDs and the analysis states of the samples and the selected sample which are on a same rack in an enlarged display area on a second display screen of the display unit in a selectable manner, and a plurality of locations of a plurality of racks, including the same rack, holding the samples in an entire process display area adjacent to the enlarged display area on the second display screen, selecting one of the racks other than the same rack from the entire process display area using a scroll bar, switching to display the second sample list as containing the sample IDs and the analysis states of the samples on the selected rack, displaying, when one of the samples in the second sample list is selected and there exists the selectable processing menu for the selected sample, a second pop-up button for the selectable processing menu for the selected sample in a sample display area of the selected sample, and a mark indicating a location of the selected sample on a pretreatment disk in a pretreatment disk display area on the second display screen, displaying, when the second pop-up button is pressed, a plurality of options of the selectable processing menu for the selected sample in a selectable manner adjacent the second pop-up button as a plurality menu buttons on the second display screen, and switching to display, when one of the menu buttons adjacent the second pop-up button is selected on the second display screen, an enlarged area of the location of the selected sample on the pretreatment disk and the analysis state of the selected sample in the enlarged display area on the second display screen of the display unit.

\* \* \* \* \*